United States Patent
Nevo

(10) Patent No.: US 6,594,517 B1
(45) Date of Patent: Jul. 15, 2003

(54) METHOD AND APPARATUS FOR GENERATING CONTROLLED TORQUES ON OBJECTS PARTICULARLY OBJECTS INSIDE A LIVING BODY

(75) Inventor: Erez Nevo, Natania (IL)

(73) Assignee: Robin Medical, Inc., Baltimore, MD (US)

( * ) Notice: Subject to any disclaimer, the term of this patent is extended or adjusted under 35 U.S.C. 154(b) by 0 days.

(21) Appl. No.: 09/700,312

(22) PCT Filed: May 12, 1999

(86) PCT No.: PCT/IL99/00250

§ 371 (c)(1), (2), (4) Date: Nov. 14, 2000

(87) PCT Pub. No.: WO99/60370

PCT Pub. Date: Nov. 25, 1999

Related U.S. Application Data

(60) Provisional application No. 60/085,652, filed on May 15, 1998.

(51) Int. Cl.$^7$ ............................ A61B 5/055; A61B 1/00
(52) U.S. Cl. .................. 600/411; 600/117; 600/145; 600/146; 600/424; 128/899
(58) Field of Search .............................. 600/411, 424, 600/114, 117, 145, 146; 128/899

(56) References Cited

U.S. PATENT DOCUMENTS

| 5,681,260 A | * | 10/1997 | Ueda et al. ............... 128/899 |
| 6,104,944 A | * | 8/2000 | Martinelli .................. 600/424 |
| 6,304,769 B1 | * | 10/2001 | Arenson et al. ........... 600/424 |

* cited by examiner

Primary Examiner—Ruth S. Smith

(57) ABSTRACT

A method and apparatus for generating a controlled torque of a desired direction and magnitude in an object within a body, particularly in order to steer the object through the body, such as a catheter through a blood vessel in a living body, by producing an external magnetic field of known magnitude and direction within the body, applying to the object a coil assembly including preferably three coils of known orientation with respect to each other, preferably orthogonal to each other, and controlling the electrical current through the coils to cause the coil assembly to generate a resultant magnetic dipole interacting with the external magnetic field to produce a torque of the desired direction and magnitude.

18 Claims, 7 Drawing Sheets

METHOD AND APPARATUS FOR GENERATING CONTROLLED TORQUES ON OBJECTS PARTICULARLY OBJECTS INSIDE A LIVING BODY

This application claims the benefit of provisional application No. 60/085,652 filed May 15, 1998.

FIELD AND BACKGROUND OF THE INVENTION

The present invention relates to a method and apparatus for generating controlled torques on objects. The invention is particularly useful for generating controlled torques in order to steer objects through a living body for purposes of performing minimally-invasive diagnostic or interventional procedures, and the invention is therefore described below with respect to such an application.

BACKGROUND

Minimally-invasive diagnostic or interventional procedures require three classes of devices—viewing devices to provide feed-back to the operator (since direct viewing as in open surgery is not available), operational devices (i.e. tools to perform the task), and controller devices which manipulate or navigate the operational devices. Most commonly, viewing devices are based on optical instrumentation with optic fibers or imaging modalities like X-ray, ultrasound, computerized tomography (CT) or magnetic resonance imaging (MRI). The operational devices vary with the procedure—endoscopes and catheters for diagnostic and interventional procedures; and miniature specialized tools for laparoscopic and other minimally-invasive interventions. The control of the devices is most commonly achieved by mechanical mechanisms. Examples include: 1) endoscopes, which are inserted into a lumen (e.g. the gastro-intestinal tract, the bronchial tree), are navigated by viewing through the endoscopes, and have mechanical control of the tip direction; 2) catheters which are inserted through blood vessels, either veins or arteries, to perform diagnostic procedures (e.g. coronary catheterization) or interventions (e.g. angioplasty of stenosed blood vessels or cardiac valves), and are navigated by mechanical manoeuvres (e.g. combinations of pushing, pulling and twisting of the external portion of the catheter) together with real-time viewing of the blood vessels and the catheters using X-ray imaging; and 3) various rigid devices for cellular aspiration, tissue biopsy, or other diagnostic and interventional procedures, which are inserted with real-time guiding (e.g. by ultrasound) or by stereotaxis guidance.

Computer-assisted stereotaxis is a valuable technique for performing diagnostic and interventional procedures, most typically with the brain. During traditional stereotaxis, the patient wears a special halo-like headframe, and CT or MRI scans are performed to create a three-dimensional computer image that provides the exact location of the target (e.g. tumor) in relation to the headframe. When this technique is used for biopsy or minimally-invasive surgery of the brain, it guides the surgeon in determining where to make a small hole in the skull to reach the target. Newer technology is the frameless technique, using a navigational wand without the headframe (e.g. Nitin Patel and David Sandeman, "A Simple Trajectory Guidance Device that Assists Freehand and Interactive Image Guided Biopsy of Small Deep Intracranial Targets", Comp Aid Surg 2:186–192, 1997).

Many of the advantages of MRI that make it a powerful clinical imaging tool are also valuable during interventional procedures. The lack of ionizing radiation, and the oblique and multiplanar imaging capabilities, are particularly useful during invasive procedures. The absence of beam-hardening artifacts from bone allows complex approaches to anatomic regions that may be difficult or impossible with other imaging techniques such as conventional CT. Perhaps the greatest advantage of MRI is the superior soft-tissue contrast resolution, which allows early and sensitive detection of tissue changes during interventional procedures. Many experts now consider MRI to be one of the most powerful imaging techniques to guide interventional interstitial procedures, and in some cases even endovascular or endoluminal procedures (Yoshimi Anzai, Rex Hamilton, Shantanu Sinha, Antonio DeSalles, Keith Black, Robert Lufkin, "Interventional MRI for Head and Neck Cancer and Other Applications", Advances in Oncology, May 1995, Vol 11 No. 2).

Virtually all current guiding and manipulation methods are based on various mechanical or electro-mechanical modules. For example, steerable catheters use tension wires to bend the tip of the catheter to the desired direction, and typically enable bending in one plane; endoscopes have mechanical control of the tip direction in two orthogonal planes, using two knobs on their control unit; rigid devices are oriented externally before they are inserted into the body to reach the defined target. The major drawback of these mechanisms is their relative complexity and high cost, which typically result with devices for multiple use.

A somewhat different approach to navigation and manipulation is based on magnetic stereotaxis. Current stereotactic procedures with rigid devices, although less invasive than open surgery, may still damage various structures along the path of insertion. The magnetic stereotaxis instrumentation (Stereotaxis Inc., St. Luis, Mo.) is less destructive. According to this technique surgeons insert a magnetic pellet the size of a rice grain into a small hole drilled into the skull of a patient, and the patient's head is then placed in a housing which contains six superconducting magnets. Using previously recorded MRI or CT images or real-time X-ray imaging as a guide, the surgeon directs the pellet through the brain by adjusting the forces of the various magnets. The pellet could tow a catheter, electrode or other device to the target. However, magnetic stereotaxis cannot be used with real-time MRI because of the MRI scanner's strong magnetic field, which precludes the use of magnetic objects inside the body during MRI scanning.

From the presented background on current methodologies, one can define the ideal system for minimal invasive procedures: It should provide real-time, 3-dimensional, non-ionizing imaging (like MRI or ultrasound) as feed-back to the user for optimal insertion and intervention; and it should implement flexible, miniaturized devices which can be manoeuvred through an optimal path to minimize damage to healthy tissues and sensitive organs.

OBJECTS AND BRIEF SUMMARY OF THE INVENTION

One object of the present invention is to provide a method and apparatus for generating controlled torques to be applied to objects, which method and apparatus are particularly useful for maneuvering miniaturized devices through an optimal path in a living body to minimize damage to healthy tissues and sensitive organs.

Another object of the present invention is to provide a method and apparatus to control and manipulate a device inside a living body through the generation of magnetic dipoles in the device which interact with an external magnetic field, like the magnetic field of an MRI system, and thus generate torque or torques for controlling and manipulating the device.

DESCRIPTION OF PREFERRED EMBODIMENTS

According to one aspect of the present invention, there is provided a method of generating a controlled torque of a desired direction and magnitude in an object within a living body, comprising: producing an external magnetic field of known magnitude and direction within the body; applying to the object a coil assembly including at least three coils whose axes are of known orientation with respect to each other and have components in the three orthogonal planes; and controlling the electrical current through the coils to cause the coil assembly to generate a resultant magnetic dipole interacting with the external magnetic field to produce a torque of the desired direction and magnitude.

According to further features in the preferred embodiment described below, the coils have axes oriented orthogonally with respect to each other; and the external magnetic field is a steady, homogenous magnetic field, particularly the main magnetic field of an MRI (Magnetic Resonance Imaging) system.

MRI is rapidly becoming the preferred methodology for minimal invasive diagnostic and interventional procedures because of its non-invasiveness, high resolution, high contrast between different soft tissues, and absence of shadowing by bones. Recent technological improvements in MRI systems provide rapid scanning sequences, which enable real-time imaging during the procedure, and an open architecture which enables access to the patient. The present invention makes use of a basic, universal component of the MRI system—the steady, homogenous magnetic field B0, typically generated by a superconducting electromagnetic coil; but the invention may also be applied with other sources of external or internal magnetic fields.

Any magnetic field exerts torque on magnetic dipoles, like the one generated by an electrical current in a closed-loop wire or a coil (Biot-Savart and Ampere Laws). The torque on the coil depends on the relative direction of the dipole with respect to the direction of the magnetic field. With at least three coils, for example three orthogonal coils, a magnetic dipole with any spatial direction can be generated: each coil generates a dipole, which can be represented by a vector, and the combined three coils generate a dipole which is the vectorial sum of the three dipoles.

One can generate such a dipole with any magnitude and direction by controlling the electrical currents through each of the three individual coils, which determine the magnitude of the dipole in each coil. If the orientation of the three coils in the magnetic field is known, a specific magnetic dipole (i.e. with specific magnitude and direction) can be generated. This controllable dipole interacts with the external magnetic field to generate a controllable torque, namely a torque with a specific magnitude and direction.

The generated torque can be used to bend the tip of a catheter or endoscope and thus to enable the operator to advance the device in the required direction. Furthermore, the torque can be used to operate various devices to perform different activities inside the body, similar to mechanical devices used during laparoscopic procedures. For example, a pliers-like clamping mechanism can be used to hold or release objects inside the body; a miniature cutting device can be used to perform remote surgery; and a miniature stapler-like device can be used to suture structures.

The present invention has significant advantages over existing methodologies. Compared with mechanical devices for navigation and operation of various diagnostic and interventional devices, electromagnetic devices constructed in accordance with the present invention for the same tasks will be smaller, cheaper, and will enable more precise control of the position, direction and operation of the device.

BRIEF DESCRIPTION OF THE DRAWINGS

The invention is herein described, by way of example only, with reference to the accompanying drawings, wherein.

DETAILED DESCRIPTION OF THE PREFERRED EMBODIMENT

The following description relates to a preferred embodiment of the invention, namely to a system for generating controllable torques in a device under MRI imaging. For the sake of simplicity, the preferred embodiment is presented with reference to the use of an MRI system's magnet field, but the invention may be implemented with other sources of external or internal magnetic fields. Potential clinical applications of the described core technology are described. In the following, vectors are underlined, to distinguish them from scalars.

Figure 1:
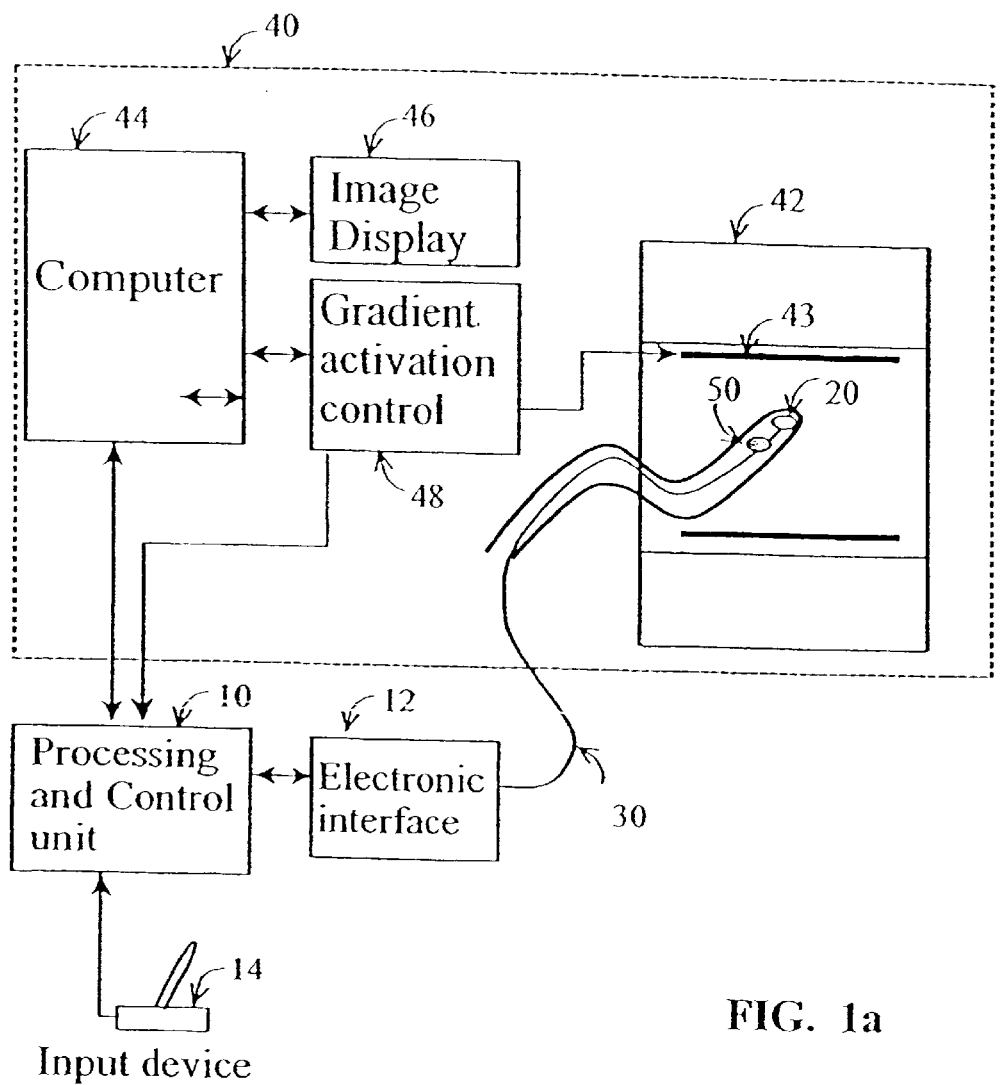
FIG. 1 is a block diagram illustrating one form of apparatus constructed in accordance with the present invention for use in an MRI system for steering an intra-body operational device in order to perform a diagnostic or interventional procedure.

The apparatus illustrated in FIG. 1 includes a processing and control unit 10, a torque-generating module (TGM) 20, which is incorporated in an intra-body device 30, and an electronic interface unit 12. The intra-body device 30 is manipulated through the interaction between the homogenous, main magnetic field (B0) of the MRI system 40, which is generated by the MRI magnet 42, and the magnetic dipoles generated by the micro-coils 22, 24, 26 in the torque-generating module 20.

Figure 1A:
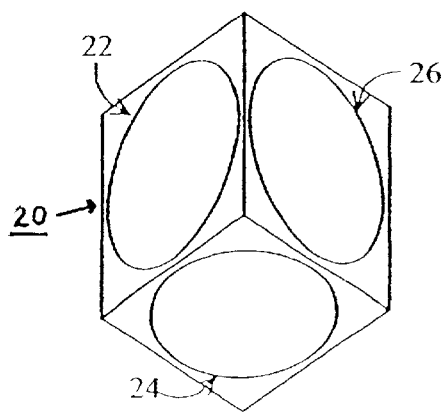
FIG. 1a more particularly illustrates one form of torque-generating module in the apparatus of FIG. 1.

The coils 22, 24, 26, as more particularly illustrated in FIG. 1a, have axes of known orientation with respect to each other, which axes have components in the three orthogonal planes. Preferably, their axes are oriented orthogonally with respect to each other as shown in FIG. 1a. As will be described more particularly below, the electrical currents through coils 22, 24, 26 may be controlled by the processing and control unit 10 to cause the torque generating module 20 to generate a resultant magnetic dipole interacting with the homogenous magnetic field produced by the MRI magnet 42 to produce a torque of the desired direction and magnitude, which is applied to the intra-body device 30, to steer it or to otherwise activate it.

The processing and control unit 10 interacts with the MRI computer 44 and with the gradient activation control unit 48 which provide the processing and control unit with information on the MRI system electro-magnetic gradient fields (B1), generated by the set of three orthogonal gradient coils 43, and the timing sequence of the activation of the these coils during MRI scanning. The MRI system provides the operator with a real-time image of the operation field through either the standard MRI display or a specialized monitor 46. An optional location and direction module (LDM) 50 may be incorporated into the intra-body device 30 to provide its location and direction or orientation.

In FIG. 1, the MRI system 40 provides the operator with a real-time display 46 of the body. The MRI computer 44 provides the processing and control unit 10 with the spatial distribution of the gradient magnetic fields as a function of time, to enable real-time localization of the device. The computer 44 also provides the processing and control unit 10 with the event schedule of the MRI system to prevent image artifacts due to the activation of the torque-generating module (TGM) 20 when the MRI gradient fields are activated for imaging. The MRI computer 44 can be programmed to perform real-time imaging of the region around the current location of the intra-body device 30 to enable fast update of the image as the device is advanced or is manipulated by the operator.

Figure 2A:
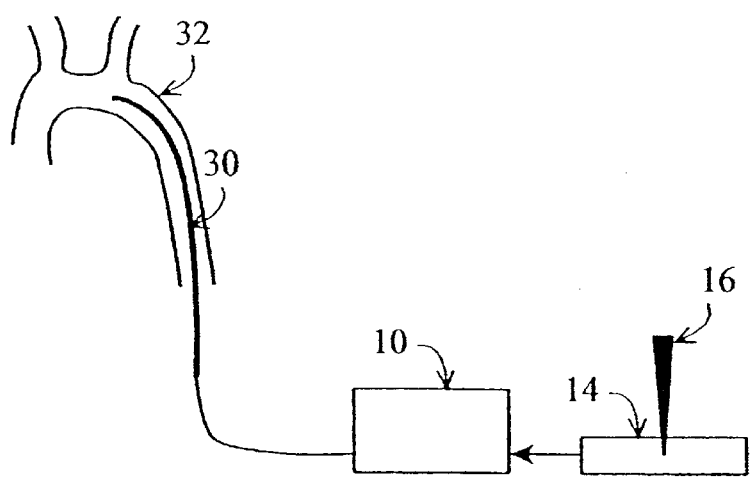
FIGS. 2a and 2b schematically illustrate the use of a joy stick for controlling the position and direction of an intra-body device, such as the tip pf a catheter, endoscope, or optical fiber, FIGS. 3a and 3b schematically illustrate the use of a joy stick with a slide for controlling the operation of an intra-body miniature tool, such as a clamping, cutting, or stapling device.
Figure 2B:
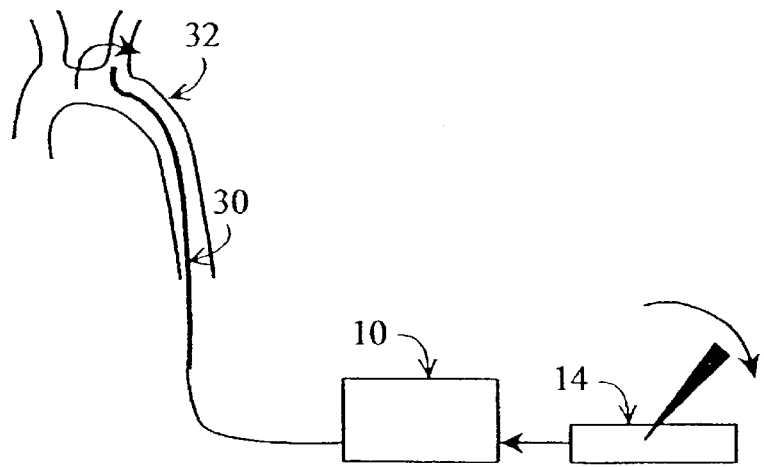

Typically, the operator manipulates the device 30 by controlling a torque on specific parts of the device, which are termed the manipulated parts. For example, FIGS. 2a and 2b illustrate how the intra-body device 30, such as a catheter, endoscope, or optical fiber, can be directed through a passageway 32, such as blood vessel bifurcations, the bronchial tree, or the gastrointestinal tract, by bending its leading tip to the required direction by manipulating a joystick 16 of an input device 14 to the processing and control unit 10.

Figure 3A:
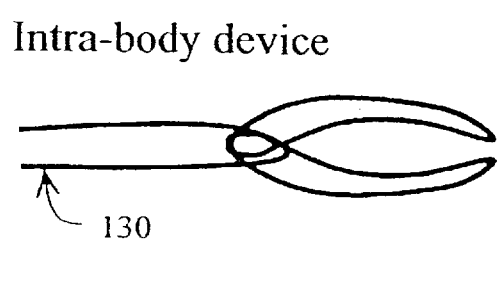
Figure 3A:
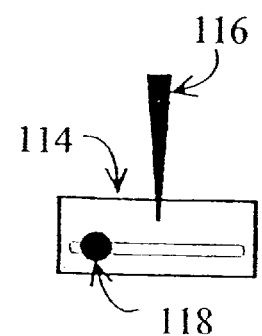
Figure 3B:
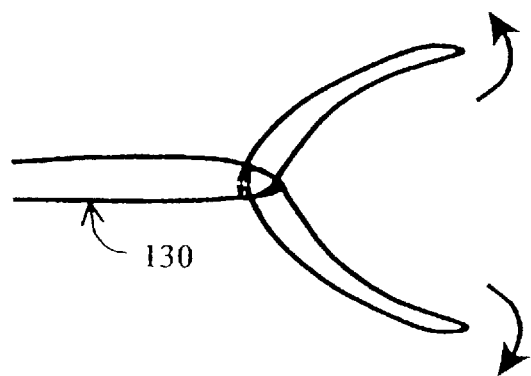
Figure 3B:
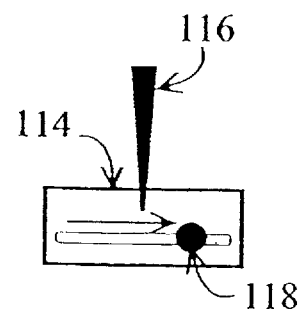

FIGS. 3a and 3b illustrate how a miniature clamp 130 can be opened or closed by exerting torques on its jaws by manipulating a slide 118 on the input device 114, which input device also includes a joystick 116 to steer the miniature clamp 130 to the proper location.

The location and direction of the intra-body device 30 (or 130) and its manipulatable parts are either measured from the MRI images, or are determined by an optional location and direction module (LDM) 50 (FIG. 1). The capability of location tracking by the MRI is available with any commercial system, provided that the intra-body device is made of material having high contrast with biological tissues (e.g. Smits HFM and Bakker CJG, "Susceptibility-Bases Catheter Visualization", in "Interventional Magnetic Resonance Imaging", edited by Debatin J F and Adams G, Springer, 1998) or has a small receiving coil which is sensitive to near-neighbourhood emitted radio-frequency signal during the MR imaging process (Dumoulin C L, Darro R D, Souza S P, "Magnetic Resonance Tracking", in "Interventional MR", edited by Jolesz F A and Young I Y, Mosby, 1998).

Figure 4:
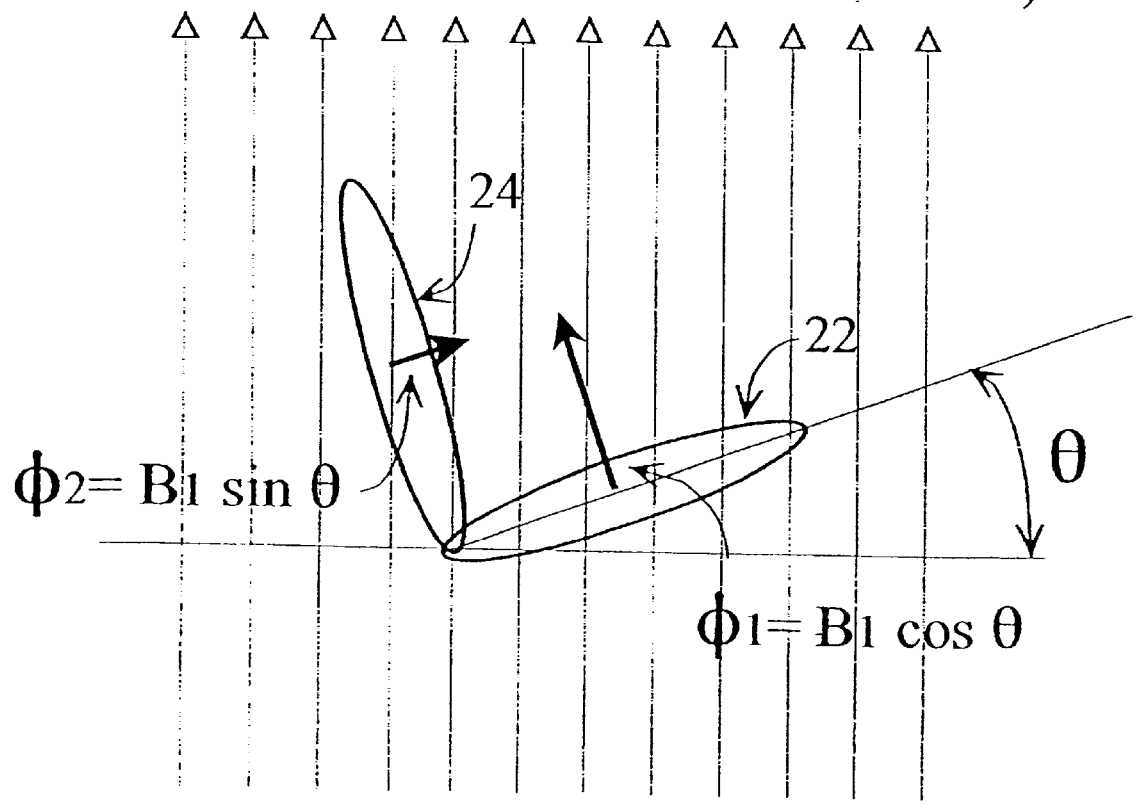
FIG. 4 is a diagram more particularly illustrating the operation of the location and direction module (LDM) in the apparatus of FIG. 1.

FIG. 4 illustrates an approach to sense the location of the device using a dedicated module, namely, the location and direction module (LDM) 50, which comprises of a set of three sensing coils. The three sensing coils may be the sane three coils 22, 24, 26 of the torque-generating module (TGM) 20, or another set of coils optimized for their use in the LDM.

The MRI alternating gradient magnetic fields (B1) induce electromotive forces (E) in the sensing coils, and the magnitudes of the induced electromotive forces are related to the magnetic flux $\Theta$ through the coil, as given by Faraday Law:

$$E = -d\Theta/dt \quad (1)$$

where the magnetic flux $\Theta$ is determined by the total magnetic field ($\underline{B}=\underline{B0}+\underline{B1}$), the coils effective area (which in a case of coil with multiple loops equals the sum of the area of all the loops in the coil), and the direction of the magnetic field with respect to the spatial orientation of the coil, which is defined by the direction of a unit vector $\underline{n}$ vertical to the coil surface:

$$\Theta = \underline{B} \cdot \underline{n} A \quad (2)$$

where the dot denotes a vectorial dot product and A is the coil area.

FIG. 4 shows how the magnitudes of the induced electromotive forces and the known magnetic field $\underline{B}$ at each point in the operating field (as supplied by the MRI system's computer) enable the calculation of the body location and direction by Equations 3 and 4, set forth below. This simplified 2-dimensional presentation of FIG. 4 includes only two measured values E1 and E2, while the full realization of the system requires three values E1, E2, E3 and the corresponding three-dimensional equations. Thus for two dimensions the direction and location will be determined by:

$$\theta = \arctan(E_2/E_1) \quad (3)$$

$$(dB/dt)^2 = E_1^2 + E_2^2 \quad (4)$$

where $\theta$ is the direction of the tip of the intra-body device 30 with respect to the magnetic field direction, and $E_1$ and $E_2$ are the induced electromotive forces in the two orthogonal coils, and B is the magnitude of the magnetic field vector $\underline{B}$. The electromotive forces are measured by electrical circuitry in the electronic interface unit 12, and the measured values are supplied to the processing and control unit 10, which calculates the direction $\theta$ and the time-derivative of the magnetic field magnitude B. Since the homogenous field B0 does not change with time, the electromotive forces are determined by the variable magnetic field B1 of the gradient coils, and equation 4 can be rewritten as:

$$(dB1/dt)^2 = E_1^2 + E_2^2 \quad (5)$$

The main advantage of the disclosed methodology—it enables sensing of the device location and direction without the need for MRI imaging, so servo control of the required manipulation of the device is feasible. Real-time control of the device may be of particular interest with some of the clinical applications as presented below.

The processing and control unit 10 receives the time-variable magnitude of the magnetic gradient fields B1 from the MRI system 40 during the activation of the gradient coils. The instantaneous location of the sensing coils is determined by the processing and control unit 10 by comparing the calculated value dB1/dt to the supplied values of the field B1, and finding the spatial location at which the calculated value of dB1/dt is equal to the generated one.

Knowing the location and direction of the intra-body device and the manipulated parts, the MRI display 46 presents this information in addition to the MR image. For example, during navigation of a catheter or endoscope, the MR image can be displayed in the device's coordinate system, as if the operator is looking forward from the device, with a synthetic representation of the tip direction. Alternatively, the image and the intra-body device can be displayed by using standard MRI views and sections. Using real-time LDM sensing enables real-time display of the device location and direction to the operator. However, other tracking methodologies can be used instead of the LDM module.

Based on the composite MRI display of the imaged body and the intra-body device, the operator manipulates the device using a standard input device 14. As described above, the direction of a catheter tip can be controlled by using a joystick 16 (FIG. 2a). The operator identifies the required direction to move the catheter by interpretation of the MR image and simply moves the joystick 16 towards the required new direction (FIG. 2b). FIGS. 3a and 3b, also described above, illustrate another example involving the operation of a clamp 130, where the operator can use the joystick 116 of input device 114 to control the direction of the clamp 130 and a slide 118 to control opening and closing of the clamp.

The commands from the input device are fed into the processing and control unit 10, which calculates the required rotation of the manipulated part in the device (e.g. the tip of a catheter or optical fiber) as determined by the input command and the current direction of this part in reference to the device (e.g. the current direction of the tip). Knowing the direction of the main magnetic field B0 of the MRI system, the processing and control unit calculates the direction of the magnetic dipole which is required to produce the torque of the required magnitude and direction to manipulate the part, for example to rotate the tip of a catheter to the new direction. The magnetic field generates a torque which rotates the magnetic dipole until it reaches an equilibrium state where the direction of the dipole aligns with the direction of the magnetic field.

Figure 5:
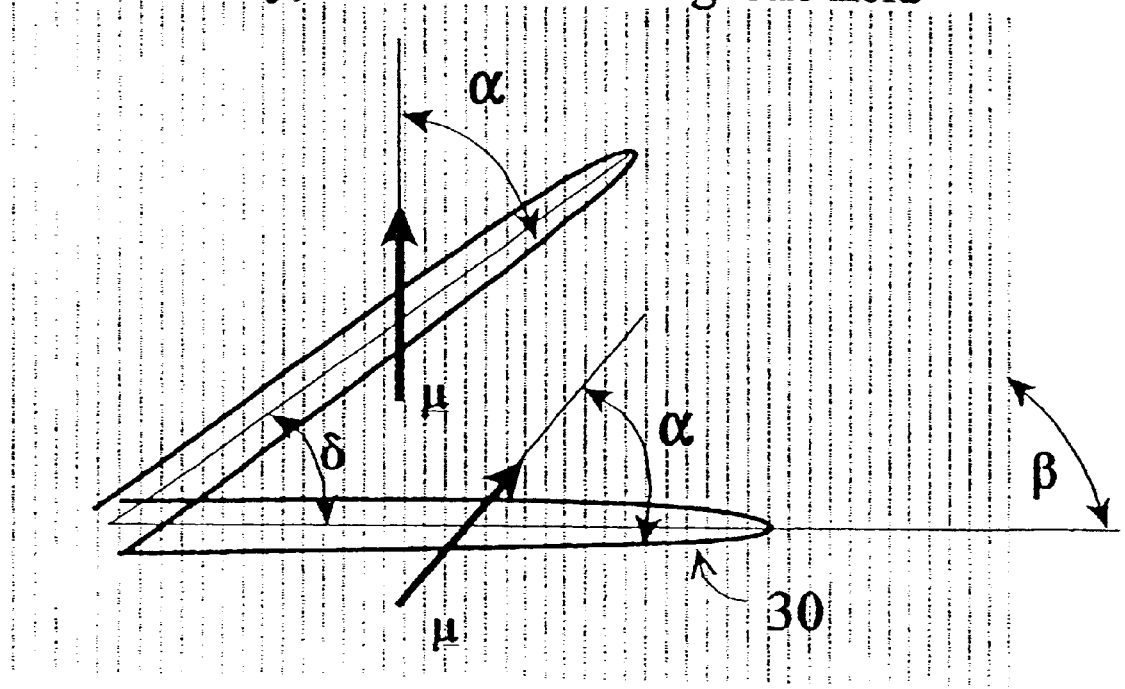
FIG. 5 is a diagram which explains our way to generate a magnetic dipole in the torque generating module in order to rotate or bend the intra-body device or part of it to a new direction.

More specifically, once the direction of the device in the MRI coordinate system is known, a plane containing the device line of direction and the magnetic field B0 line of direction is determined. Referring now to FIG. 5, which presents this plane, the angle between the magnetic field direction and the current direction of the device 30 is denoted β. For the sake of simplicity in the presentation, the desired direction of the device, as determined by the input from the input device 14. is presented in the same plane (i.e. this is a simplified 2-dimensional case) and forms an angle δ with the current direction of the device. In order to bend the tip of the device to the new direction defined by the angle δ, a dipole is generated in a direction α, with respect to the current direction of the device, where the angle α given by:

$$\alpha = \beta - \delta \quad (6)$$

If the angle α is maintained throughout the steering maneuver, the magnetic dipole $\underline{\mu}$ interacts with the magnetic field B0 to generate a torque which bends the device until it aligns with the desired direction, at that time the dipole aligns with the direction of the magnetic field B0 and the resultant torque diminishes to zero. Other implementations can be used, like using a variable dipole direction which maximizes the generated torque to induce faster bending or rotation of the tip. If a real-time feedback is available by using the LDM 50, then optimal control of the manipulation can be achieved by using servo control of the dipole generation (e.g. by PID controller).

Figure 6A:
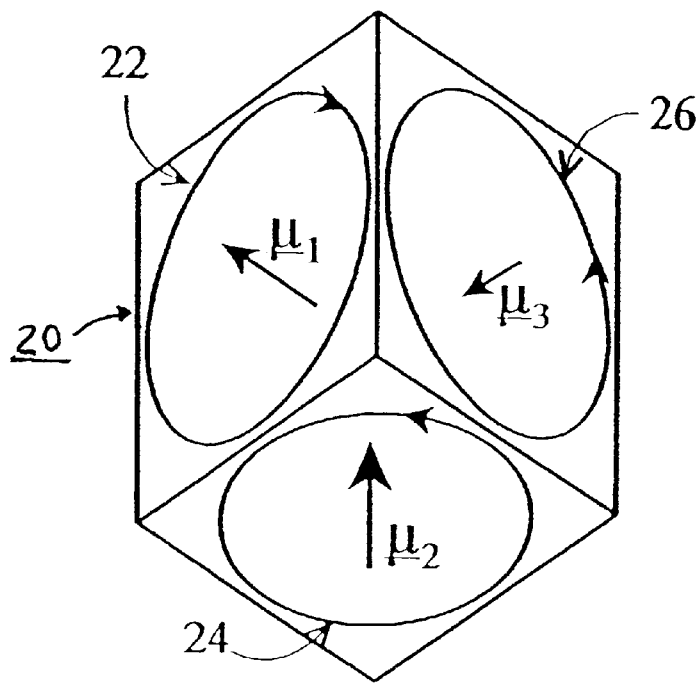
FIGS. 6a and 6b diagrammatically illustrate, in a simplified two-dimensional display, the manner of creating a specific magnetic dipole by summing the dipoles generated by three orthogonal coils.
Figure 6B:
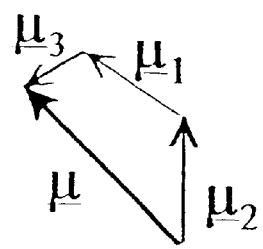

Referring now to FIG. 6a, the magnetic dipole in the torque-generating module (TGM) 20 is generated in the required direction by controlling electrical currents in the three micro-coils 22, 24, 26 of the TGM. The preferred embodiment is with three orthogonal coils, however other configurations with one, two, or more than three coils can be used for specific applications.

The net dipole in the TGM is calculated by vectorial sum of the three individual magnetic dipoles which are generated by the three coils 22, 24, 26:

$$\underline{\mu} = \underline{\mu}_1 + \underline{\mu}_2 + \underline{\mu}_3 \quad (7)$$

The high intensity homogenous magnetic field B0 of the MRI system interacts with the magnetic dipole and generates a torque on the activated part of the device, e.g. the tip of the catheter, endoscope, or optical fiber:

$$\underline{\tau} = \underline{\mu} \hat{x} \underline{Bo} \quad (8)$$

where $\underline{\tau}$ is the generated torque, $\underline{\mu}$ is the magnetic dipole, $\hat{x}$ is the vectorial cross product and $\underline{Bo}$ is the vectorial representation of the magnetic field B0 of the MRI system.

The manipulated part bends or rotates into the required direction and thus enables the operator to conduct the required task, for example to navigate the device through an optimal path to minimize damage to tissue or into a bifurcation in blood vessel or another lumen. In most MRI systems the steady, homogenous uni-directional magnetic field B0 limits the possible directions of the generated torque to off-axial directions. For example, for MRI system with magnetic field in the Z-direction (the body axial direction), a device positioned in the two transverse directions can be bent in one plane and rotated around its axial direction, while a device positioned in the Z-direction can be bent in any direction but cannot be rotated. Although this may impose some limitations on the operation of the device, correct planning of the procedure, for example choosing the insertion point of the device, can overcome this limitation. Furthermore, any direction can be achieved by combining two manipulations in the effective directions. For example, to bend the tip in the Y direction, the tip can be initially bent in the X direction and then the device can be rotated by 90 degrees. Other potential solutions include the combination of mechanical manipulation mechanisms with the present invention to achieve an unlimited spatial manoeuverability or the use of an electromagnet to add a magnetic field in transverse direction to the main MRI magnetic field.

During the manipulation of the device, the MRI system may continue scanning the body. To prevent distortion of the image due to the magnetic field of the generated dipole, the processing and control unit suspends the operation of the torque-generating module when the MRI system activates the gradient fields and is sensitive to small distortions of the magnetic field geometry. With fast MRI scanners these pauses are relatively short and may not be sensed by the operator. The continuous real-time imaging enables the continuous update of the image with the device in it for optimal performance by the system's operator.

Figure 7:
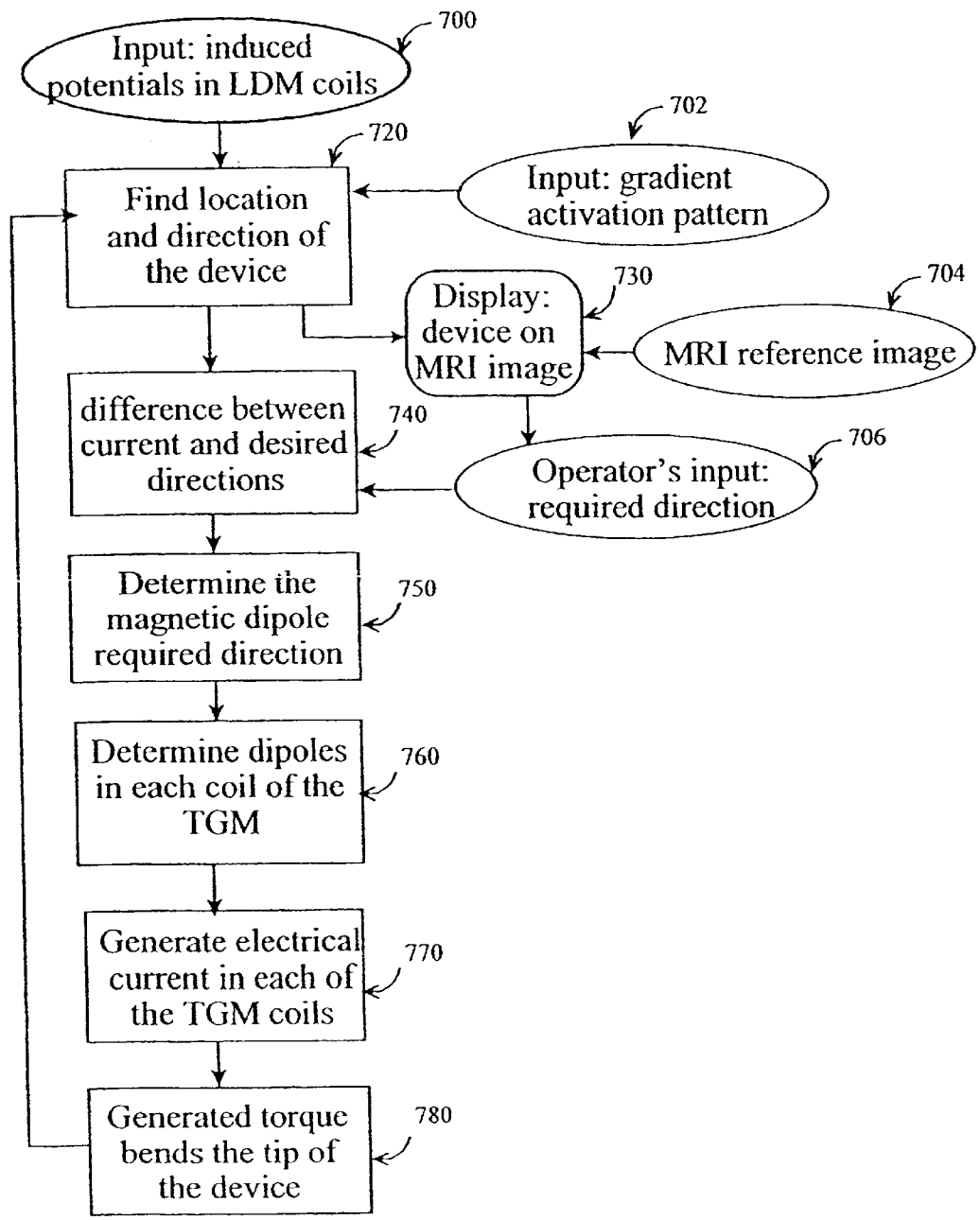
FIG. 7 illustrates the functioning of the invention in steering a device during MRI imaging.

FIG. 7 is a flow chart illustrating the operation of the processing and control unit 10, FIG. 1. First the patient undergoes a baseline MRI scanning of the region of interest (ROI) to be used as a reference image 704. The operator inserts the device into the body and advances it into the ROI.

The location and direction variables 720 in the MRI coordinate system are determined by the processing and control unit 10 by processing input signals 700 from the LDM during activation of the gradient fields of the MRI system. The location and direction variables 720 are used to generate a composite image 730 of the device on the reference image 704.

The operator then determines the new direction of the device and provides the desired direction 706 as a command from the input device to the processing and control unit 10. The processing and control unit calculates the difference 740 between the current direction of the device and the desired direction of the device. The processing and control unit determines the required direction of the magnetic dipole 750 by using Equation 6.

The magnitude of the required dipole is determined by technical and safety constraints, for example the maximal permitted heating of the coils. The processing and control unit calculates the required dipoles 760 in the three coils of the TGM, using the determined magnitude and direction of the required magnetic dipole and the current direction of the device. The processing and control unit activates drivers to generate electrical currents in the three coils in order to result with the required dipoles in the three coils 770. The generated dipole interacts with the magnetic field B0 of the MRI and bends the tip of the device 780. At the same time the operator can move the device, for example to push it into a new location.

The process is now repeated, the new location and orientation 720 are determined and the updated location of the device on the reference image is presented to the operator to continue the steering of the device.

If high precision is required, or to enable the use of the invention with a dynamic ROI (e.g. moving ROI due to breathing or cardiac contraction), the device manipulation can be sequenced with rapid MRI scans which are used to refresh the baseline MRI image 704 and to provide a dynamic reference image.

Potential clinical applications of the invention include the navigation of various instruments through various organs, cavities or lumens in the body to perform either diagnostic or therapeutic interventions. The invention can be used to navigate instruments through the pulmonary system (the bronchial tree or blood vessels), the cardiovascular system (heart chambers, blood vessels), the gastro-intestinal tract (stomach, duodenum, biliary tract, gall bladder, intestine, colon), the liver, the urinary system (bladder, ureters, kidneys), the skeletal system (joints), the genital organs, the brain (internally through the ventricles or blood vessels or externally through a burr hole in the scull). The invention enables navigation through these organs to reach a specific location and to perform diagnostic procedures (e.g. biopsy, aspiration, direct viewing) and therapeutic procedures (e.g. local drug delivery, ablation, cryo-therapy, gene delivery, etc.).

For example, the invention may be implemented in the following devices:

1. Steerable catheters—the torque-generating modules (TGM) can replace the complex and costly tension wires used to manipulate the tip of steerable catheter and enable mass production of low-cost, single use steerable catheters.
2. Flexible endoscope—as with the steerable catheters, the TGM can replace the currently used mechanical system of controlling the endoscope tip and enable cheaper and thinner endoscope. Furthermore, the use of an input device like a joystick rather than two separate knobs will enable easier operation of the endoscope.
3. Rigid endoscope—a flexible, sliding tip with TGM can be integrated into the rigid endoscope to enable final, precise navigation inside the target, after it was inserted with the rigid endoscope, or to enable the application of specific intervention in multiple directions without the need to move the rigid device.
4. Optic fibers for laser therapy—the TGM can be used to control the direction of the fiber's tip and enable more accurate laser therapy under MRI control.

While the invention has been described with respect to several preferred embodiments, it will therefore be appreciated that these are set forth merely for purposes of example, and that many other variations, modifications and applications of the invention may be made.

What is claimed is:

1. A method of generating a controlled torque of a desired direction and magnitude in an object within a body, comprising:

producing an external magnetic field of known magnitude and direction within said body, said magnetic field having a coordinate system;

applying to said object a coil assembly including at least three coils whose axes are of known orientation with respect to each other, and have components in three orthogonal planes;

tracking the orientation of said object with respect to the coordinate system of said external magnetic field;

applying an electrical current and controlling the electrical current through said coils to cause the coil assembly to generate a resultant magnetic dipole interacting with said external magnetic field to produce a torque of said desired direction and magnitude.

2. The method according to claim 1, wherein said body and said object are imaged on a display during the steering of the object within said body.

3. The method according to claim 1, wherein said step of producing an external magnetic field comprises producing an external magnetic field by an MRI (Magnetic Resonance Imaging) system, and wherein said step of tracking comprises using the gradient fields of said MRI system as a reference field for tracking.

4. A method of steering a medical device through a passageway within a body, comprising:

producing an external magnetic field of known magnitude and direction within said body, said magnetic field having a coordinate system;

providing a medical device located within said body;

applying to said medical device at least one coil;

tracking the orientation of said medical device with respect to the coordinate system of said external magnetic field;

applying an electrical current and controlling the electrical current through said coil to cause it to generate a resultant magnetic dipole interacting with said external magnetic field to produce a torque steering said medical device in a desired direction.

5. The method according to claim 4, wherein said step of producing an external magnetic field comprises producing an external magnetic field by an MRI (Magnetic Resonance Imaging) system.

6. The method according to claim 5, wherein said step of tracking comprises using the gradient fields of said MRI system as a reference field for tracking.

7. Apparatus for generating a controlled torque of a desired direction and magnitude to be applied to an object within a body, comprising:
- means for producing an external magnetic field of known magnitude and direction within said body, said magnetic field having a coordinate system;
- an object adapted to be located within said body;
- a coil assembly attached to said object and including at least three coils whose axes are of known orientation with respect to each other, and have components in three orthogonal planes;
- means for tracking the orientation of said object with respect to the coordinate system of said external magnetic field;
- and a drive system for applying controlled electrical current trough said coils to cause the coil assembly to generate a resultant magnetic dipole interacting with said external magnetic field to produce a torque of said desired direction and magnitude.

8. The apparatus according to claim 7, wherein said coils have axes oriented orthogonally with respect to each other.

9. The apparatus according to claim 7, wherein said external magnetic field is a steady, homogenous magnetic field.

10. The apparatus according to claim 7, wherein said object is a medical device to be steered by said controlled torque through a path within a living body to perform a diagnostic or interventional procedure.

11. The apparatus of according to claim 10, wherein said medical device is selected from the group consisting of a catheter, endoscope, or optical fiber.

12. The apparatus according to claim 10, wherein said medical device is a biopsy or surgical tool.

13. The apparatus according to claim 7, wherein said apparatus further includes an MRI system having a display for imaging said body and said object during the steering of the object through said body.

14. The apparatus according to claim 7, wherein said means for producing an external magnetic field comprises an MRI (Magnetic Resonance Imaging) system, and wherein said means for tracking comprises the gradient fields of said MRI system as a reference field for tracking.

15. Apparatus for steering a medical device through a passageway within a body, comprising:
- a medical device adapted to be located within said body;
- means for producing an external magnetic field of known magnitude and direction within said body;
- at least one coil attached to said medical device;
- means for tracking the orientation of said medical device with respect to the coordinate system of said external magnetic field;
- and a drive system for applying controlled electrical current through said coil to cause the coil to generate a resultant magnetic dipole interacting with said external magnetic field to produce a torque steering said medical device in a desired direction.

16. The apparatus according to claim 15, wherein said coil is a part of a coil assembly having at least two coils whose axes are of known orientation with respect to each other and have components in at least two different orthogonal planes.

17. The apparatus according to claim 16, wherein said coil assembly includes three coils having axes oriented orthogonally with respect to each other.

18. The apparatus according to claim 15, wherein said means for producing an external magnetic field comprises an MRI (Magnetic Resonance Imaging) system.

* * * * *